United States Patent [19]
van Muiden

[11] Patent Number: 5,639,409
[45] Date of Patent: Jun. 17, 1997

[54] METHOD FOR MANUFACTURING A TUBULAR EXTRUSION

[75] Inventor: Johannes Gerardus Maria van Muiden, Peize, Netherlands

[73] Assignee: Cordis Corporation, Miami Lakes, Fla.

[21] Appl. No.: 369,789

[22] Filed: Jan. 6, 1995

[30] Foreign Application Priority Data

Jan. 7, 1994 [NL] Netherlands .................. 94.00031

[51] Int. Cl.$^6$ .................................................. B29C 47/24
[52] U.S. Cl. .................. 264/108; 264/167; 264/171.28; 264/171.29; 264/209.2; 264/312; 425/133.1; 604/264
[58] Field of Search ........................ 264/167, 209.2, 264/171.29, 171.28, 312, 108; 425/133.1; 604/264

[56] References Cited

U.S. PATENT DOCUMENTS

| | | | |
|---|---|---|---|
| 2,779,970 | 2/1957 | Stocker . | |
| 3,416,982 | 12/1968 | Petzetakis | 264/171.29 |
| 3,520,966 | 7/1970 | Soffiantini | 264/171.29 |
| 3,606,636 | 9/1971 | Glass et al. . | |
| 3,933,960 | 1/1976 | Cameron et al. | 264/171.29 |
| 5,059,375 | 10/1991 | Lindsay | 264/209.2 |
| 5,156,785 | 10/1992 | Zdrahala | 264/209.2 |
| 5,244,619 | 9/1993 | Burnham | 264/171.29 |
| 5,258,160 | 11/1993 | Utsumi et al. | 264/209.8 |
| 5,335,410 | 8/1994 | Burnham | 264/171.29 |

FOREIGN PATENT DOCUMENTS

| | | | |
|---|---|---|---|
| 0102422 | 3/1984 | European Pat. Off. | 264/149 |
| 1555590 | 1/1969 | France . | |
| 279074 | 2/1952 | Switzerland . | |

Primary Examiner—Jeffery R. Thurlow
Attorney, Agent, or Firm—Thomas R. Vigil

[57] ABSTRACT

The method for manufacturing a tube-like extrusion profile includes the steps of: simultaneously conveying a number of, in the circumferential direction of the profile, divided streams of material of at least two different compositions to a molding-nozzle; and, making the streams flow together in the molding-nozzle. At least one of the streams is supplied rotating in a circumferential direction. Preferably at least two streams of material are supplied rotating in opposite directions, so that at least two helically shaped bands of material extend in opposite directions in the extrusion profile. The method also includes the step of: allowing the combined streams of material to cool off into the extrusion profile so that the streams of material supplied in a rotating manner extend helically in the extrusion profile formed by the method.

9 Claims, 3 Drawing Sheets

FIG.1

METHOD FOR MANUFACTURING A TUBULAR EXTRUSION

BACKGROUND OF THE INVENTION

1. Field of the Invention

The invention relates to a method for manufacturing a tube-like extrusion profile with a desired combination of properties, in particular with regard to flexibility, torsional stiffness and pressure resistance. More specifically, the present invention relates to the extrusion of a tube with helically extending bands of other material than the base material of the tube. These helically extending bands can be of harder material so that the stiffness properties of the tube can be improved and by using two helical bands with opposed directions, a substitute for braided reinforcement is obtained.

2. Description of the Prior Art

Catheters used for angiographic purposes, for instance, comprise a tube-like basic body which must have a good torsional stiffness in order to be able to manipulate the catheter properly. Furthermore, this material should have a high compression resistance to allow, for example, the introduction of contrast medium under high pressure via the catheter.

The usual catheters of this type, therefore, comprise a braided reinforcing layer of metal wire, providing the required properties.

With the continuing trend towards ever thinner catheters, it is becoming increasingly difficult and expensive to manufacture a suitable tube-like basic material in this way.

Heretofore various wire reinforced catheters and methods for making same have been proposed and analogous and nonanalogous examples of some of these tubular body constructions, e.g., catheters, and methods for making same are disclosed in the following U.S. Patents and foreign patent publications:

| U.S. Pat. No. | Patentee |
| --- | --- |
| 2,779,970 | Stöcker |
| 3,606,636 | Glass et al. |
| 3,426,744 | Ball |
| 3,618,613 | Schulte |
| 3,752,617 | Burlis et al. |
| 4,044,765 | Kline |
| 4,050,411 | Kimmich |
| 4,073,287 | Bradely et al. |
| 4,176,662 | Frazer |
| 4,276,250 | Satchell et al. |
| 4,665,604 | Dubowik |
| 4,705,511 | Kocak |
| 4,776,334 | Prionas |
| 4,840,186 | Lekholm et al. |
| 4,945,342 | Steinemann |
| 4,947,866 | Lessar et al. |
| 5,112,304 | Barlow et al. |
| 5,324,275 | Raad et al. |
| 5,279,596 | Castenada et al. |

British Published Patent Application
  UK Patent Appl. No. 1,349,843 to Creators Ltd.
  UK Patent Appl. No. 2,218,580 to Nogami et al.
EP Published Patent Application
  EP Pub. No. 0 249 338 to Spector et al
French Patents
  French Patent No. 1,555,590 to Labarre et al.
  French Patent No. 2,649,642 to Figuere et al.

German Patent Publications
  DE 19 38 720 (Offenlegungsschrift) to Kalwar
Swiss Patents
  Swiss Patent No. 279,074 to Dätwyler

SUMMARY OF THE INVENTION

The object of the invention is to provide a method for manufacturing a tube-like extrusion profile with a desired combination of the properties referred to above.

This aim is achieved with a method for manufacturing a tube-like extrusion profile, comprising the steps of:

simultaneously conveying a number of, in the circumferential direction of the profile, divided streams of material of at least two different compositions to a moulding-nozzle;

making the streams flow together in the moulding-nozzle whereby at least one of the streams is supplied in a circumferential direction rotating manner;

supplying at least two streams of material rotating in opposite directions, so that at least two helically shaped bands of material extend in opposite directions in the extrusion profile; and, allowing the combined streams of material to cool off into the extrusion profile so that the streams of material supplied in a rotating manner extend helically in the extrusion profile.

The helically shaped band of material formed in the extrusion profile can, for instance, be made of a stiffer material than the basic material, so that a good compression resistance and reliable torsional stiffness can be achieved.

Also, a very good torsional stiffness in both directions can be obtained, which for an intended application as basic material for a catheter is most desirable.

With the at least two streams of material being supplied rotating alternately to and fro at such an angle that the streams of material at least touch each other, a reticulated pattern of bands of material in the basic material is obtained. Thus, a great flexibility can be combined with a high torsional stiffness.

An advantageous embodiment includes supplying the at least two streams of material supplied in a rotating manner at different diameters. Each of the obtained helically shaped bands of material extends uninterrupted but, because of the combined effect of the helically shaped bands of material in the different layers, a good torsional stiffness and compression resistance is nevertheless obtained.

By varying the relation between the rotation velocity and the extrusion velocity in the longitudinal direction of the profile for at least one of the streams of material supplied in a rotating manner, a consequent helically shaped stream of material in the extrusion profile has a varying pitch. In this way the relation between the torsional stiffness and bending stiffness can be varied. In general, a large pitch of the helical line results in a lower torsional stiffness but a higher bending stiffness and vice versa. Furthermore, a tube-like extrusion profile with a large pitch of the helically shaped bands of material extends less easily in a longitudinal direction.

In general, the distal end of a catheter should be very pliable to prevent trauma. Additional increase in or reduction of the pliability can be achieved by turning on and/or off at least one of the streams of material in a controlled manner during the extrusion.

To enhance the properties of the material of the streams of material added in a rotating manner, fibers can be added to the material supplied as a rotating stream. Doing so, the modulus of elasticity can be increased significantly.

The invention relates to and also provides a catheter made of a tube-like extrusion profile according to the teachings of the invention, comprising at least one section of which the wall comprises helically shaped bands of material of varying composition.

The invention will be explained in greater detail in the following description with reference to the attached drawings.

DESCRIPTION OF THE PREFERRED EMBODIMENT(S)

Figure 1:
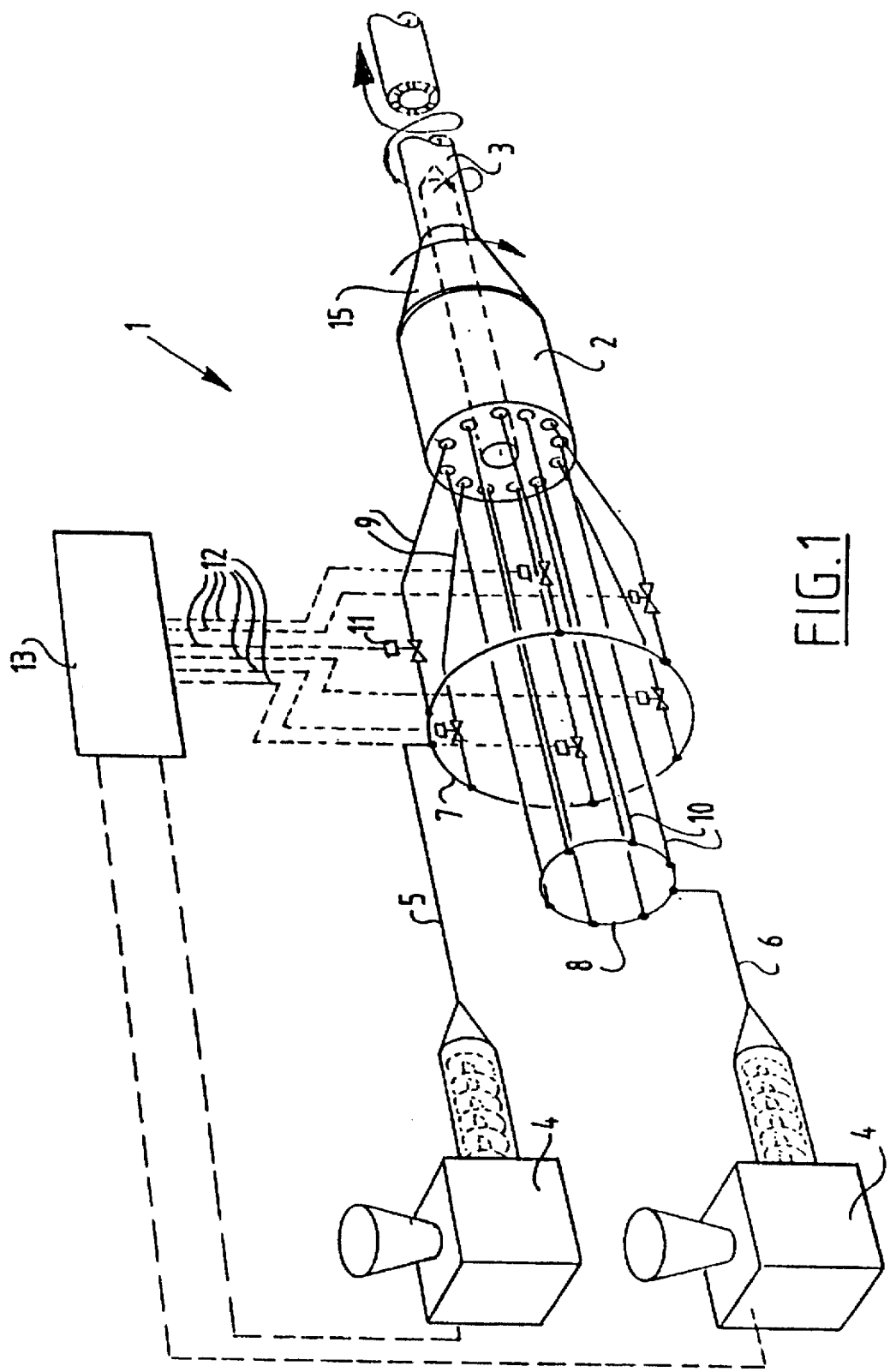
FIG. 1 shows schematically the method according to the invention.

FIG. 1 shows schematically an extrusion device which can be used to carry out the method of the invention. This device 1 comprises a moulding-nozzle 2, inside of which the extrusion profile 3 is formed. The embodiment of the method, as described here, involves the use of streams of material of two different compositions. Each of the materials is brought in an extruder 4 in the for extrusion required correct degree of liquidity and at the right pressure. The material coming from the first extruder is conveyed, through a line 5, to a distribution line 7. From this distribution line a number of lines 9 branch off, each of which can convey a stream of material.

The second extruder 4 leads to a line 6 also connected to a distribution line 8 which, in its turn, links up with a number of lines 10 conveying separate streams of material.

As FIG. 1 shows, there are in this embodiment twelve, in the circumferential direction of the tube-like profile 3 distributed streams of material of two different compositions. The different materials can be incorporated in a pattern of alternate bands in the wall of the profile 3.

The streams of material conveyed through the lines 9 and 10 flow together in the moulding-nozzle 2. This moulding-nozzle 2 comprises a schematically indicated rotating section 15 through which the streams of material are supplied rotating in a circumferential direction. After allowing the combined stream of material to cool off in the usual manner, the extrusion profile 3, comprising bands of material extending a helical pattern, has been formed. The extrusion profile formed will be explained in greater detail below, with reference to FIG. 2.

In each of the lines 9, conveying the streams of material of the first composition, cut-off valves 11 have been arranged. Each of these cut-off valves 11 can be controlled by means of control lines 12 by a control means 13. The control means 13 can open or close the cut-off valves 11 during the extrusion process in a controlled manner and consequently the streams of material conveyed through the corresponding lines 9 can be turned on and off in a similar controller manner. The control means 13 can be made to control the extruders 4, as well. The opening and closing of the cut-off valves 11 is preferably programmed in a preset cycle. Manual operation is obviously possible, as well.

In the embodiment, as shown in FIG. 1, the streams of material through the lines 10 are conveyed continuously and those through the lines 9 can be turned on and off in a controlled manner by the cut-off valves 11.

Figure 2:
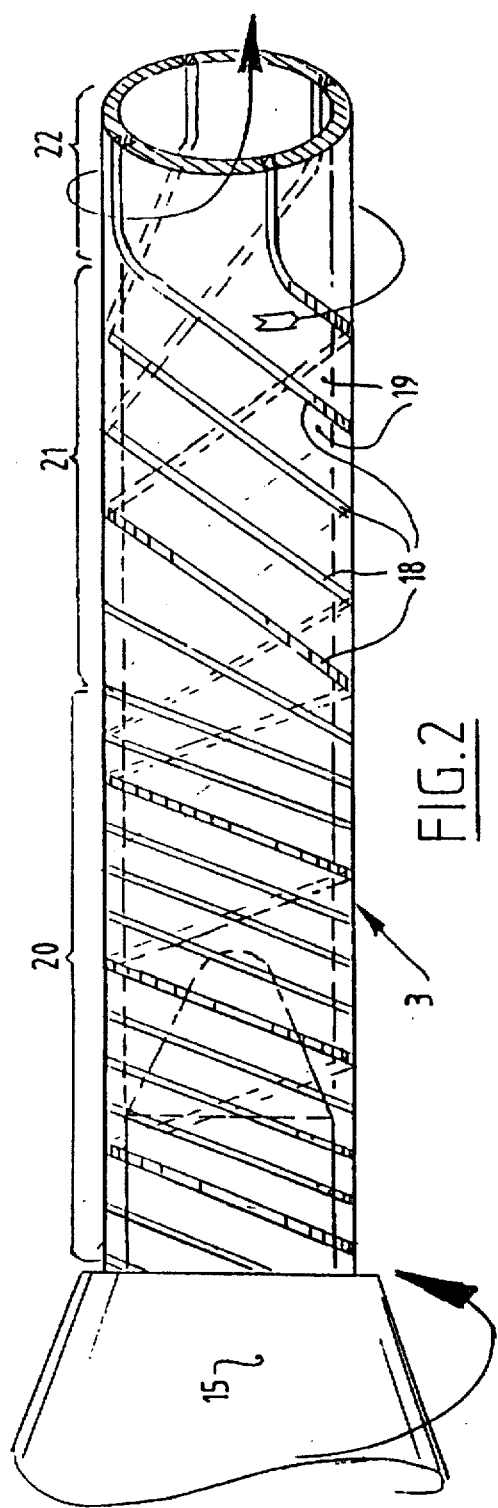
FIG. 2 illustrates an extrusion profile manufactured by the method according to the invention.

FIG. 2 shows, somewhat simplified, the extrusion profile obtained. As the streams of material are supplied in a rotating manner, the helically shaped bands of material 18 mentioned before, are formed in the extrusion profile 3. These have been incorporated in a basic material 19. For the sake of clarity, only four helically shaped bands of material have been drawn in FIG. 2, while six of them are formed with the setup, as shown in FIG. 1.

In FIG. 2 it has also been indicated schematically, that by altering the relation between the rotation velocity and the extrusion velocity, a variation in the pitch in the longitudinal direction of the profile can be arranged. In the part 22 drawn on the right-hand side, no rotation has been applied and consequently the streams of material extend parallel to the longitudinal direction. In the adjacent part 21, a rotation has been applied at a limited velocity, so that a relatively small pitch of the helically shaped bands is obtained. The section 20 on the left, has been formed at a relatively high rotation velocity, resulting in a large pitch angle.

In case the helically shaped bands of material 18 are made of a stiffer material than the basic material 19, the part 20 of the extrusion profile formed, will have a relatively high torsional stiffness and low bending stiffness, while the section 22 will have a relatively high bending stiffness and low torsion rigidity. By varying the above-mentioned relation between the rotation velocity and extrusion velocity, the properties of the extrusion profile can be adjusted.

In addition to adjusting the properties of the extrusion profile by varying the angle of the helical line, the properties can also be varied, of course, by controlling the supply of the different streams of material as described.

Figure 3:
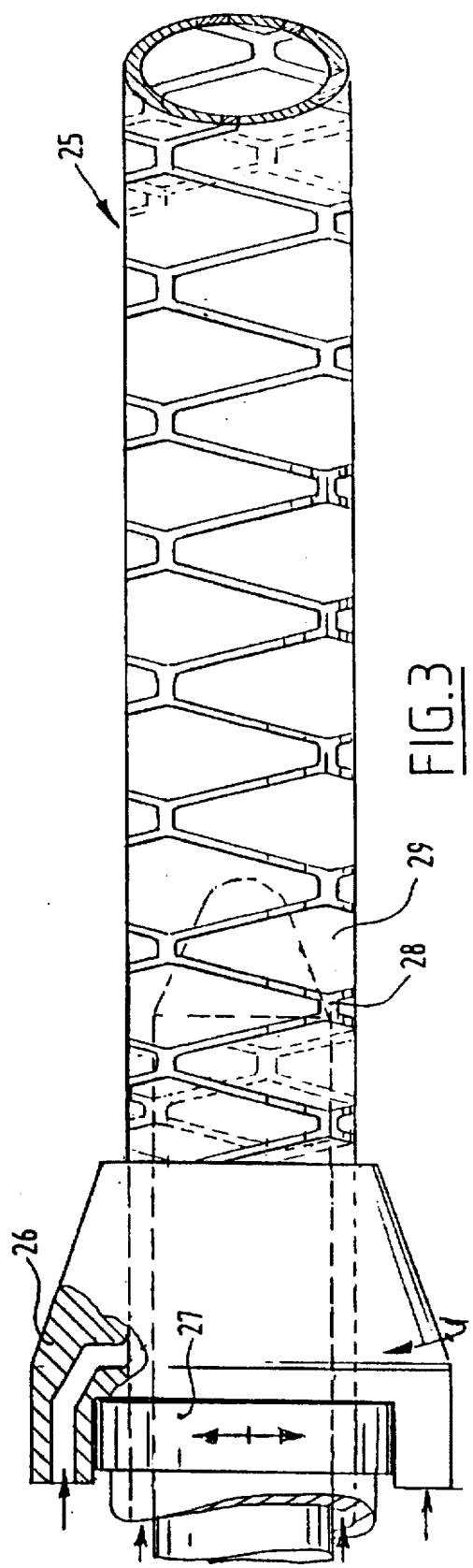
FIG. 3 shows an alternative embodiment of the method according to the invention.

FIG. 3 illustrates another embodiment of the method according to the invention. In this case, two streams of material are supplied rotating in opposite directions. This has been indicated with two rotating parts 26, 27 of the extrusion nozzle. The at least two streams of material are supplied rotating alternately to and fro at such an angle that the streams of material touch each other. With the profile 25 of FIG. 3 a relative rotation of 90° occurs. With the reversal of motion, the two parts of the extrusion nozzle are stationary for a very short period, and the two streams of material from the different nozzles mix, resulting in the reticulated pattern of the interconnected helically shaped streams of material, as illustrated in FIG. 3. If the material 28 of the helically shaped bands of material is stiffer than the basic material 29, the extrusion profile 25 thus obtained will display a good torsional stiffness combined with a reasonable pliability. The pressure resistance will be excellent.

Figure 4:
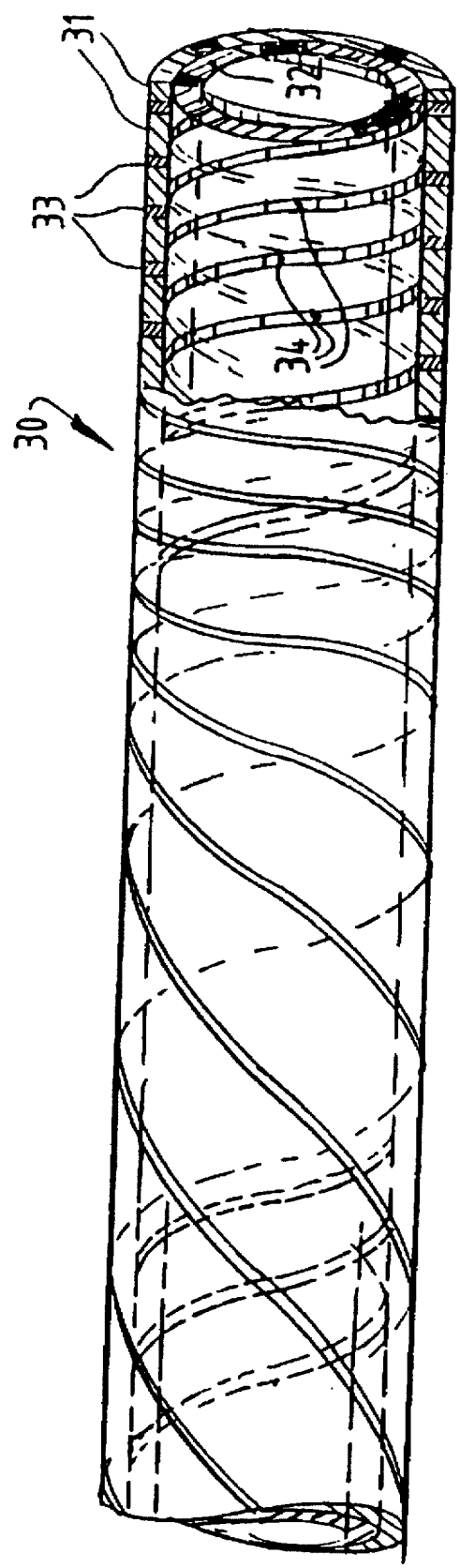
FIG. 4 shows an extrusion profile manufactured by another embodiment of the method.

The extrusion profile 30 shown in FIG. 4 can be obtained with an embodiment of the method according to the invention developed to a greater degree.

The extrusion profile 30 is made up of two coaxial layers 31, 32. In each of the layers 31, 32 a number of helically shaped bands of material have been extruded. The helically shaped bands of material 33 in the outermost layer 31 are running in the opposite direction to the helically shaped bands of material 34 in the inmost layer 32 of the extrusion profile. The two layers with the helically shaped layers of material formed inside, can be manufactured in one extrusion movement. In that case, a good bond between the inner layer and the outer layer can be simply ensured by a choice of the right combination of materials of the two coaxial layers.

By an alternative method, it is also possible, however, to manufacture the inside layer 32 first and to arrange the outer layer 31 around it subsequently, for instance, by extruding the latter onto the inner layer 32.

As FIG. 4 illustrates, the pitch of the helically shaped bands of material varies in the longitudinal direction of the extrusion profile. This variation has been effected in the manner described above by varying the relation between the rotation velocity and the extrusion velocity.

By varying the pitch of the different layers of material in the way described, if desired in combination with selectively turning on and off a number of streams of material, a great variety in properties along the length of the piece of extrusion profile can be obtained. Because of this the entire length of the tube-like basic body of the catheter, for instance, a catheter used for angiographic purposes, can be manufactured in one operation. Separately fixing pliable distal end sections or compression resistant proximal end sections, respectively, has therefore become superfluous.

Although, in each of the figures a number of helically shaped layers of material are shown, a preferred embodiment of the method of the invention employes two helically shaped bands of material wound in opposed directions.

The material for the profile is chosen in accordance with the intended application. In this way, one can choose, when manufacturing an extrusion profile for a catheter as mentioned before, a soft polyurethane, polyethene, polyamide, etc. as basic material and a stiff plastic material from the same group for the helically shaped bands of material. One can also add a fibrous material, for instance, aramide fibers or liquid crystal polymers, to the material used for the helically shaped bands. This will increase the modulus of elasticity of this material significantly.

It will be clear that through flow control of the streams of material the bands of material, which are referred to as the helically shaped bands of material in the above, will gradually take on certain proportions, such that it would be better to call these the basic material. For the method according to the teachings of the invention, there can be, no essential difference between the basic material and the material of the helically shaped bands of material.

I claim:

1. Method for manufacturing a tubular extrusion, comprising the steps of:

simultaneously conveying a number of, in the circumferential direction of the tubular extrusion, divided streams of material of at least two different compositions to a moulding-nozzle;

making the two streams flow together in the moulding-nozzle whereby at least one of the streams is supplied in a rotating circumferential direction;

supplying at least two streams of material rotating in opposite directions, so that at least two criss-crossing helically shaped bands of material extend in opposite directions in the tubular extrusion; and, allowing the combined streams of material to cool off into the tubular extrusion so that the streams of material supplied in a rotating manner extend helically, across each other, in the tubular extrusion.

2. Method according to claim 1, including the step of supplying the at least two streams of material rotating alternately to and fro at such an angle that the streams of material at least touch each other in the tubular extrusion.

3. Method according to claim 1, including the step of supplying the at least streams of material supplied in a rotating manner at different diameters.

4. Method according to claim 1, including the step of varying the relation between the rotation velocity and the extrusion velocity in the longitudinal direction of the tubular extrusion for at least one of the streams of material supplied in a rotating manner, so that the consequently helically shaped stream of material in the extrusion profile has a varying pitch.

5. Method according to claim 1, including the step of turning on and/or off at least one of the two streams of material in a controlled manner during the extrusion process.

6. Method according to claim 1, including the step of choosing a soft plastic material from the class consisting essentially of: polyurethane, polyethene and polyamide for the basic material and choosing a hard plastic material from the class consisting essentially of: polyurethane, polyethene and polyamide for the material supplied as a rotating stream.

7. Method according to claim 6, including the step of adding fibers to the material supplied as a rotating stream.

8. Method according to claim 7, wherein the fibers are chosen from the class consisting essentially of aramide fibers and liquid crystal polymer plastic-containing materials.

9. Method according to claim 1, including the step of: reversing the motion of rotation of the streams such that the two streams remain stationary for a very short period of time and mix together resulting in a short longitudinal pattern of the interconnected streams in the tubular extrusion.

* * * * *

UNITED STATES PATENT AND TRADEMARK OFFICE
CERTIFICATE OF CORRECTION

PATENT NO. : 5,639,409
DATED : June 17, 1997
INVENTOR(S) : Johannes Gerardus Maria van Muiden It is certified that error appears in the above-indentified patent and that said Letters Patent is hereby corrected as shown below:

Column 3, line 31, "extruder is" should be --extruder 4 is--.

Column 6, line 17, "least streams" should be --least two streams--.

Signed and Sealed this

Ninth Day of September, 1997

Attest:

BRUCE LEHMAN

*Attesting Officer*  *Commissioner of Patents and Trademarks*